(12) United States Patent
Kotab

(10) Patent No.: US 8,615,164 B1
(45) Date of Patent: Dec. 24, 2013

(54) SYSTEMS AND METHODS FOR OPERATION OF RECORDING DEVICES SUCH AS DIGITAL VIDEO RECORDERS (DVRS)

(76) Inventor: Dominic M. Kotab, San Jose, CA (US)

( * ) Notice: Subject to any disclaimer, the term of this patent is extended or adjusted under 35 U.S.C. 154(b) by 9 days.

(21) Appl. No.: 13/081,438

(22) Filed: Apr. 6, 2011

Related U.S. Application Data

(60) Provisional application No. 61/321,441, filed on Apr. 6, 2010.

(51) Int. Cl.
*H04N 5/76* (2006.01)

(52) U.S. Cl.
USPC ........... 386/299; 386/292; 386/293; 386/294; 386/295; 386/296; 386/297

(58) Field of Classification Search
USPC .................................. 386/291–295, 297–299
See application file for complete search history.

(56) References Cited

U.S. PATENT DOCUMENTS

| | | | |
|---|---|---|---|
| 7,917,008 B1 * | 3/2011 | Lee et al. ...................... | 386/291 |
| 8,006,263 B2 * | 8/2011 | Ellis et al. ....................... | 725/38 |
| 8,046,801 B2 * | 10/2011 | Ellis et al. ....................... | 725/58 |
| 8,588,590 | 11/2013 | Kotab | |
| 2008/0022012 A1 | 1/2008 | Wang | |
| 2008/0112686 A1 | 5/2008 | Chen et al. | |
| 2009/0046988 A1 | 2/2009 | Kenagy | |
| 2009/0238543 A1 | 9/2009 | Guo | |
| 2009/0257733 A1 | 10/2009 | Ellis | |
| 2009/0310937 A1 | 12/2009 | Ellis et al. | |
| 2010/0119208 A1 | 5/2010 | Davis et al. | |
| 2010/0135639 A1 | 6/2010 | Ellis et al. | |
| 2010/0202754 A1 * | 8/2010 | Bhogal et al. ................... | 386/83 |
| 2011/0085781 A1 * | 4/2011 | Olson .......................... | 386/296 |
| 2011/0150431 A1 * | 6/2011 | Klappert ....................... | 386/296 |

OTHER PUBLICATIONS

U.S. Appl. No. 13/083,415, filed Apr. 8, 2011.
U.S. Appl. No. 13/081,446, filed Apr. 6, 2011.
U.S. Appl. No. 12/362,966, filed Jan. 30, 2009.
Non-Final Office Action from U.S. Appl. No. 13/083,415 dated Apr. 1, 2013
Restriction/Election Requirement from U.S. Appl. No. 13/083,415 dated Jan. 22, 2013.
Restriction/Election Requirement from U.S. Appl. No. 13/081,446 dated Nov. 9, 2012.
Non-Final Office Action from U.S. Appl. No. 13/081,446 dated Jan. 14, 2013.
Notice of Allowance and Fee(s) Due from U.S. Appl. No. 13/081,446 dated Sep. 9, 2013.
Final Office Action from U.S. Appl. No. 13/083,415 dated Oct. 25, 2013.
Notice of Allowance from U.S. Appl. No. 13/081,446 dated Sep. 9, 2013.
Supplemental Notice of Allowance from U.S. Appl. No. 13/081,446 dated Oct. 16, 2013.
U.S. Appl. No. 14/054,775, filed Oct. 15, 2013.
U.S. Appl. No. 14/054,779, filed Oct. 15, 2013.

\* cited by examiner

*Primary Examiner* — Helen Shibru
(74) *Attorney, Agent, or Firm* — Zilka-Kotab, PC

(57) ABSTRACT

A system, method, and computer program product are provided according to one embodiment. The method includes receiving a request to record a television program; determining an amount of available storage space on each of at least two recording devices; and selecting one of the recording devices to store a representation of the television program on a computer readable medium associated with the respective recording device based on the determined amounts of available storage space on each of the at least two recording devices, wherein the selected recording device stores the representation of the television program. Additional systems, methods, and computer program products are also presented.

23 Claims, 12 Drawing Sheets

SYSTEMS AND METHODS FOR OPERATION OF RECORDING DEVICES SUCH AS DIGITAL VIDEO RECORDERS (DVRS)

RELATED APPLICATIONS

This application claims priority to U.S. Provisional Patent App. No. 61/321,441, filed Apr. 6, 2010, which is herein incorporated by reference.

BRIEF DESCRIPTION OF THE DRAWINGS

For a fuller understanding of the nature and advantages of the present invention, as well as illustrative modes of use, reference should be made to the following detailed description read in conjunction with the accompanying drawings.

Figure 1:
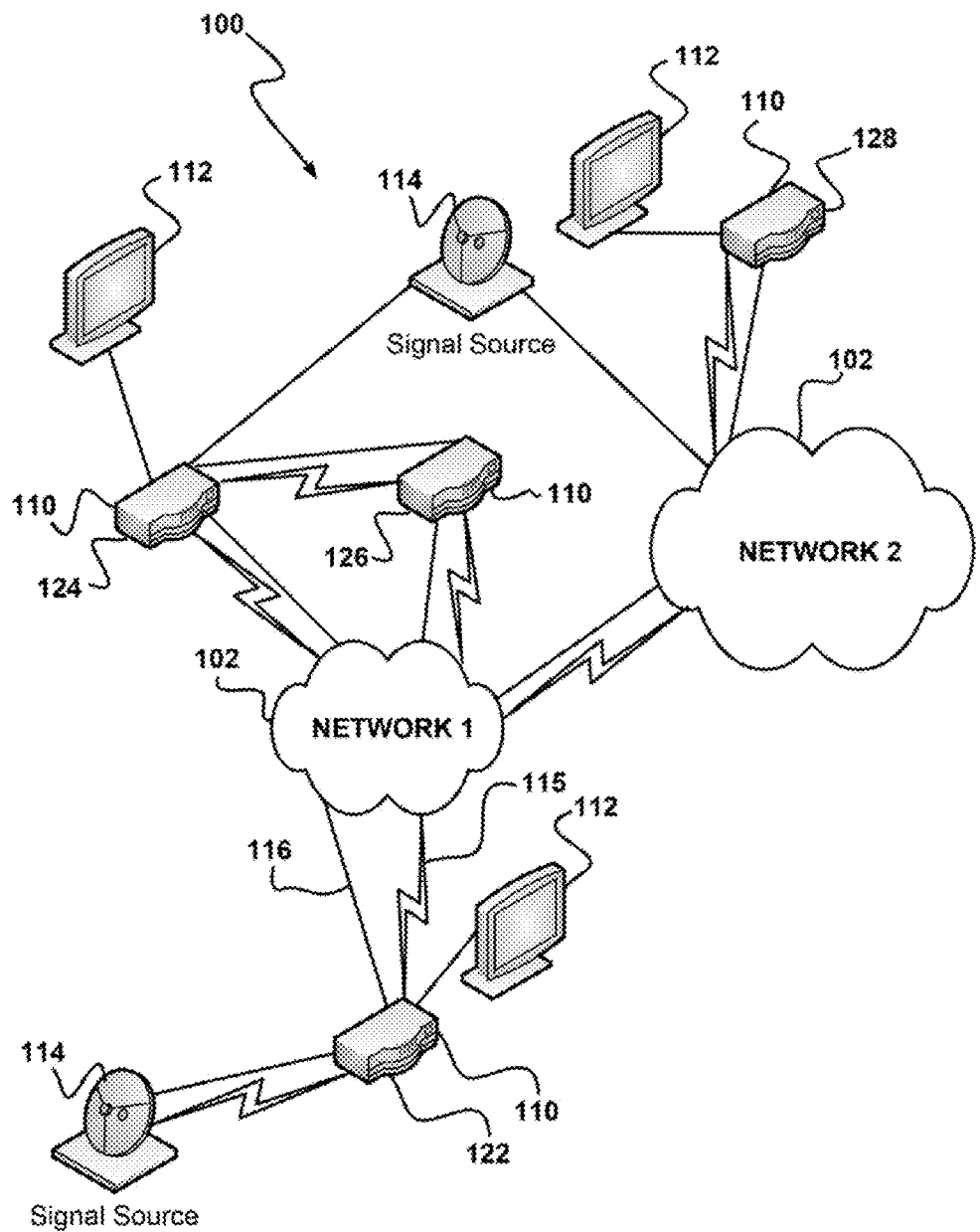
FIG. 1 is a schematic diagram of a network system, showing multiple recording devices capable of communicating with each other, according to one embodiment.

Various embodiments of the present invention are described in further detail below with reference to the figures, in which like items are numbered the same in the several figures.

DETAILED DESCRIPTION

The following paragraphs describe certain features and combinations of features that can be used in connection with each of the methods of the invention and embodiments, as generally described below. Also, particular features described hereinafter can be used in combination with other described features in each of the various possible combinations and permutations. As such, the invention is not limited to the specifically described embodiments.

Unless otherwise specifically defined herein, all terms are to be given their broadest possible interpretation and scope including one or more meanings implied from the specification as well as one or more meanings understood by those skilled in the art and/or as defined in dictionaries, treatises, etc.

The following description is made for the purpose of illustrating the general principles of the present invention and is not meant to limit the inventive concepts claimed herein. Further, particular features described herein can be used in combination with other described features in each of the various possible combinations and permutations.

It must also be noted that, as used in the specification and the appended claims, the singular forms "a," "an" and "the" include plural referents unless otherwise specified.

In one general embodiment, a system, method, and computer program product are provided. The method includes receiving a request to record a television program; determining an amount of available storage space on each of at least two recording devices; and selecting one of the recording devices to store a representation of the television program on a computer readable medium associated with the respective recording device based on the determined amounts of available storage space on each of the at least two recording devices, wherein the selected recording device stores the representation of the television program. Additional systems, methods, and computer program products are also presented.

In another general embodiment, a system, method, and computer program product are provided. The method includes receiving a request to record a television program; determining an amount of storage space needed to record previously-scheduled television programs on a first recording device; determining an amount of storage space needed to record previously-scheduled television programs on a second recording device; selecting one of the recording devices to store a representation of the television program on a computer readable medium associated with the respective recording device based on the determined amounts of needed storage space on each of the recording devices, wherein the selected recording device stores the representation of the television program. Additional systems, methods, and computer program products are also presented.

In yet another general embodiment, a system, method, and computer program product are provided. The method includes receiving a request to record a television program; determining whether recording the television program conflicts with a previously-scheduled recording on a first recording device; scheduling recording of the television program on the first recording device if the recording does not conflict with a previously-scheduled recording on the first recording device; sending a request to schedule recording of the television program on a second recording device if the recording conflicts with a previously-scheduled recording on the first recording device. Additional systems, methods, and computer program products are also presented.

In yet another general embodiment, a system, method, and computer program product are provided. The method includes determining an amount of available storage space on each of at least two recording devices; transferring stored video data from a first of the recording devices to a second of the recording devices having more available storage space than the first of the recording devices, wherein the video data is stored on the second recording device and made available for later output, wherein the video data is deleted from the first recording device. Additional systems, methods, and computer program products are also presented.

In yet another general embodiment, a system, method, and computer program product are provided. The method includes receiving a request to transfer a stored representation of a television program from a first recording device to a second recording device, the first and second recording devices communicating with each other using a direct connection between the recording devices or over a local area network to which they are directly coupled; transferring the stored representation from the first recording device to the second recording device, wherein the representation is stored on the second recording device and made available for later output. Additional systems, methods, and computer program products are also presented.

In yet another general embodiment, a system, method, and computer program product are provided. The method includes receiving a request to record a television program; determining an amount of available storage space on each of at least two recording devices; outputting the amounts of available storage space on each of the recording devices; outputting a request for selection of one of the recording devices for recording the television program; receiving a reply to the request for selection, the reply indicating a selection of one of the recording devices; and instructing the selected recording device to record the television program. Additional systems, methods, and computer program products are also presented.

In yet another general embodiment, a system, method, and computer program product are provided. The method includes determining an amount of available storage space on a first recording device; determining that a size of video data associated with a present or future recording operation exceeds the amount of available storage space; selecting previously-stored video data for transfer to a second recording device; transferring the selected video data from the first recording device to the second recording device, wherein the transferred video data is stored on the second recording device and made available for later output; and deleting the selected video data from the first recording device.

FIG. 1 is a schematic diagram of a network including multiple recording devices, such as Digital Video Recorder (DVRs), according to one embodiment. The network architecture 100, in accordance with, one embodiment, may include a plurality of networks 102. In the context of the present network architecture 100, the networks 102 may each take any form including, but not limited, to a local area network (LAN), a wireless network (e.g., Wi-Fi) or link (e.g., Bluetooth), a wide area network (WAN) such as the Internet, cable television network, telephony network, peer-to-peer network, etc. In addition, more than one network may be included under each network 102. Moreover, the architecture 100 shown may include more or fewer components than those shown, in various embodiments. Also, wireless links 115 and hardwired links 116 are shown to illustrate that a connection may include one or both types of links 115, 116, as discussed below.

Coupled to at least one of the networks 102 is a plurality of recording devices 110. In this example, several recording devices are present, namely a first DVR 122 and a second DVR 124, and potentially a third and fourth DVR 126, 128. The recording devices may communicate with each other via the networks 102. Also, or alternatively, some or all of the recording devices may communicate with each other directly, as shown for DVRs 124 and 126. Any communication protocol may be used in such communication, including protocols known in the art. The information communicated between the recording devices may include one or more of video data from a signal source, video data stored on the recording device, video files, pictures, audio, etc.

Furthermore, each recording device 110 is capable of being placed in communication with a display 112. The display 112 may be a television, a computer monitor, a video projector, or any type of display.

Figure 2:
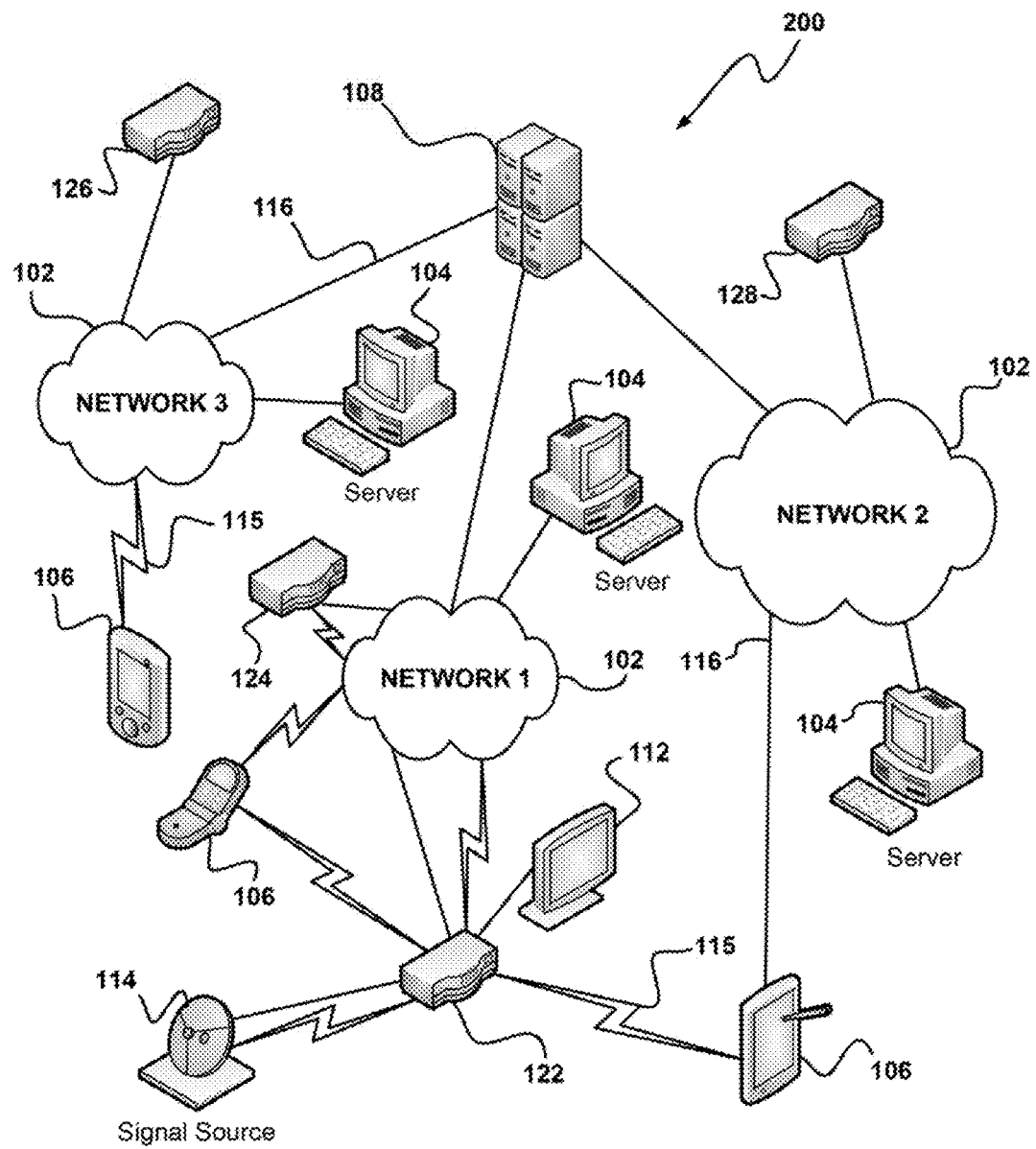
FIG. 2 is a schematic diagram of a network system, showing multiple recording devices capable of communicating with each other, according to another embodiment.

FIG. 2 is a schematic diagram of a network architecture including multiple recording devices and various handheld devices and servers according to one embodiment. The network architecture 200, in accordance with one embodiment, may include a plurality of networks 102, and various features of the architecture 100 of FIG. 1. In the context of the present network architecture 200, the networks 102 may each take any form including, but not limited, to a local area network (LAN), a wireless network (e.g., Wi-Fi) or link (e.g., Bluetooth), a wide area network (WAN) such as the Internet, cable television network, telephony network, peer-to-peer network, etc. in addition, more than one network may be included under each network 102. Moreover, the architecture 200 shown may include more or fewer components than those shown, in various embodiments.

Coupled to the networks 102 are servers 104 which are capable of communicating over the networks 102. Also coupled to the networks 102 and the servers 104 is a plurality of clients 106. Such servers 104 may include a mainframe computer, network appliance, desktop computer, lap-top computer, hand-held computer, mobile phone, smart phone, and other types of mobile media devices (with or without telephone capability), personal digital assistant (PDA), peripheral (e.g. printer, etc.), any component of a computer, and/or any other type of logic. In order to facilitate communication among the networks 102, at least one gateway 108 is optionally coupled therebetween. The at least one gateway 108 may be a router, server, computer, etc., configured such that communications between connected devices is enacted (possibly faster, easier, with different operating systems, etc.).

The communication lines 115 indicate wireless connections, while the communication lines 116 indicate hardwired connections. These communication types are shown for illustrative purposes only, and should in no way limit the scope of the invention, e.g., any connection can be hardwired, wireless or a combination of both. For instance, a client 106 may communicate with a network 102 wirelessly 115, as shown in Network 1, or a client 106 may communicate with a network 102 via hardwired connections 116, as shown in Network 2.

A hardwired connection may be any connection which uses a wire, cord, cable, etc., to connect devices together and allow communications between such devices. Some illustrative hardwire connections include Ethernet, serial, USB, parallel, FIREWIRE, etc. A wireless connection may be any connection which uses a wireless communication technique with which to communicate between two or more devices, possibly over a distance. Some illustrative wireless connections include radio frequency (RF) communication (such as Wi-Fi, Bluetooth, W-LAN, mobile telephony network-3G, CDMA, etc.), microwave communication, satellite communication (such as Global Positioning Satellite—GPS), infrared (IR) communication, etc.

In the context of the network architecture 100, a recording device 110, such as a Digital Video Recorder (DVR), computer system, tape-based recording system, network storage system, network-accessible peripheral storage system such as a USB drive coupled to a computer, etc., may be integrated and/or employed in the network architecture 100 that is capable of recording video content, transmitting content via wireless and/or wired techniques, and communicating with various handheld devices wirelessly and through network communications such as wireless telephone systems, Bluetooth, Wi-Fi, etc. As shown, the recording device 110 may be placed in communication with a network 102 either wirelessly or through hardwiring, or be placed in communication with a client 106, such as a handheld device, wirelessly. Additionally, the recording device 110 may be any type of device that is capable of receiving and recording video data, such as a digital video recorder (DVR), a computer with a TV-in card, an iPOD, an iPHONE, a BLACKBERRY device, a SLINGBOX device, etc. A recording device may include additional functionality, such as Internet access, wireless networking, external memory storage interface, etc. The recording device may be a standalone unit or integrated with an intermediary device, such as a cable receiver, set top box, satellite receiver, etc.

In particularly preferred embodiments, the methods set forth herein are performed by a recording device.

Furthermore, the recording device 110 is capable of being placed in communication with a display 112. The display 112 may be a television, a computer monitor, a video projector, or any type of display. Such connection may be a direct connection, connection via network, connection via an additional device or devices, etc., and combinations thereof. In addition, the recording device 110 is capable of being placed in communication with a signal source 114. The signal source 114 may include any entity or device capable of providing a video signal to the recording device 110. For example, the signal source 114 may be an antenna receiving a signal from a television tower, a satellite signal, a satellite signal receiver, a satellite antenna, a video camera, a cable company's transmitter, a cable box, a digital set top box, a computer broadcasting network, another receiving device, etc.

In some embodiments, the recording device 110 may be placed in communication with a client 106. The client 106 may include a desktop computer, lap-top computer, hand-held computer, mobile phone, personal digital assistant (PDA) network appliance, computer readable memory, digital music player, peripheral (e.g. printer, etc.), any component of a computer, and/or any other type of logic. The client 106 may communicate with the recording device 110 wirelessly.

More information regarding functionality of a recording device 110 with other devices such as client 106, servers 104, etc. can be found in U.S. patent application Ser. No. 12/491,954 to Kotab, filed Jun. 25, 2009, which is herein incorporated by reference.

Several methods will now be described. As an option, such methods may be implemented in the context of the architecture and environment of FIGS. 1 and/or 2. Of course, however, the methods may be carried out in any desired environment. Moreover, operations from the various methods may be combined in any desired manner to provide additional embodiments and permutations of the present invention.

Figure 3:
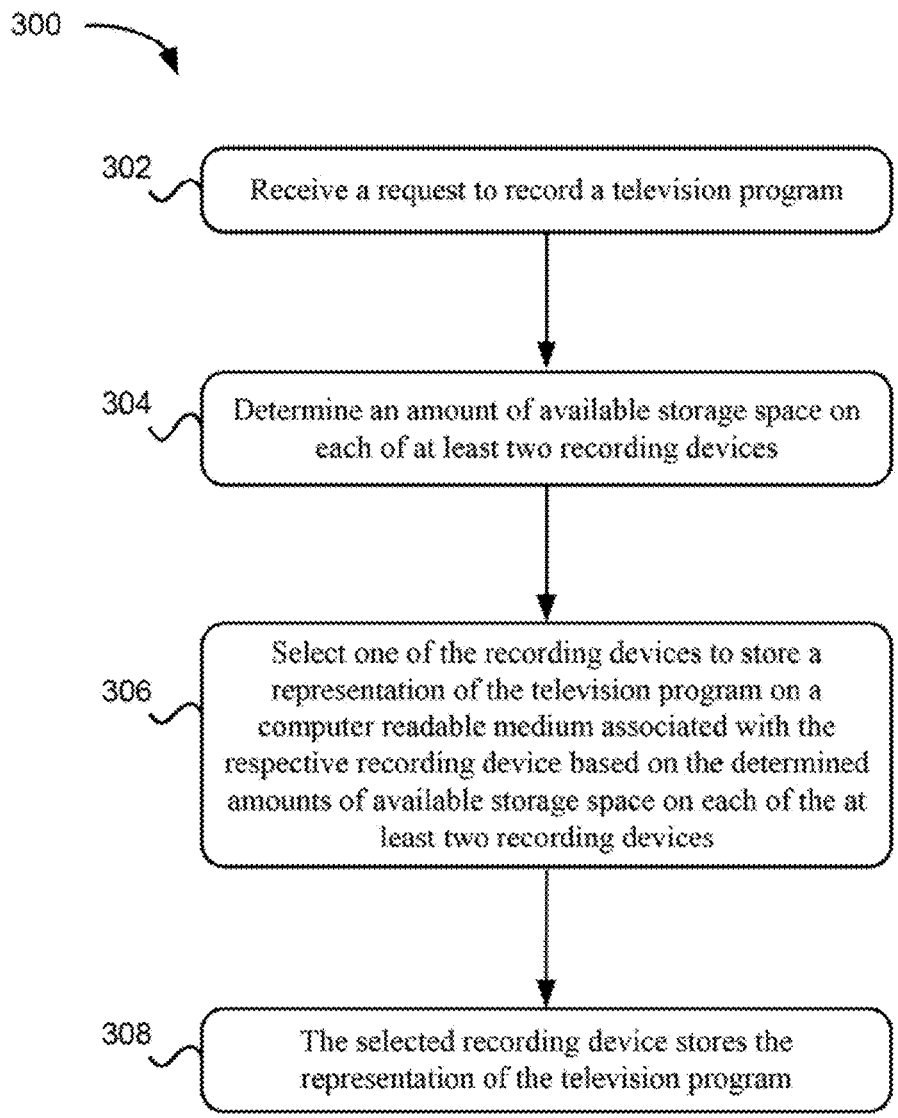
FIG. 3 is a flowchart depicting a system according to one embodiment.

A method 300 according to one embodiment depicted in FIG. 3 includes, or a system according to one embodiment has logic for, receiving a request to record a television program (the television program may include a single program, a series of programs, a special program, etc.). See operation 302. The request may be received by one of the recording devices, a local server, a remote server, a website, a webpage, a workstation, a television, etc. This request to record a television program may be initiated on a handheld device (such as a mobile telephone, a personal media player (such as an APPLE iPOD, a MICROSOFT ZUNE, a BLACKBERRY device, etc.), a universal remote control, etc.), on the Internet (such as through a website, a webpage, an email program, etc.), directly through a user interface with a recording device, etc. Moreover, any method may be used to receive a request to record a television program, including receiving selection of a program from a guide output on a display device, website, webpage, etc.; receiving an instruction as a result of a search query; receiving a calendared request to record the program, etc. Additional examples, which may be implemented in various embodiments, are disclosed in U.S. patent application Ser. No. 12/612,559 to Kotab, filed Nov. 4, 2009, and which is herein incorporated by reference.

Further, the television program may be any type of programming related to television, in some approaches. For example, the television program may be from subscription programming, pay-per-view (PPV) programming, public broadcast programming, television programs broadcast over the Internet, YOUTUBE television content, iTUNES store television content, Internet-based original content, streaming programs from HULU or NETFLIX, etc. Furthermore, the television program may be formatted in any manner, such as by any of the following standards from the Motion Picture Editors Guild (MPEG, MPEG-2, MPEG-4). DivX, Xvid, FFmpeg, Windows Media Video (WMV), National Television System Committee (NTSC), Advanced Television Systems Committee (ATSC), THEORA, QuickTime (.mov), Audio Video Interleave (AVI), high definition (HD) 3D standards, etc.

The television program may be received through hardwired and/or wireless connections. Further, the connections may include an intermediary device, such as a cable box, a set top box, a satellite antenna box, another device (such as a video cassette recorder (VCR), digital video disc (DVD) player/recorder, BLU-RAY player/recorder, camcorder, gaming console—such as SONY PLAYSTATION 3, MICROSOFT XBOX, etc.), an aerial antenna, a computer equipped with a TV-in card, a network, appliance, etc. This intermediary device may receive the television program from a service provider, such as a cable television service, a satellite television service provider, an online content provider, an Internet service provider, a website, a webpage, etc.

In some embodiments, the intermediary device may receive the signal from a remote source or from a local receiver. For example, in one embodiment, a cable box may receive a digital or analog television signal through a coaxial cable. In another embodiment, a satellite dish may receive a digital or analog television signal from a satellite transmitter. In yet another embodiment, a network appliance may receive a digital signal from a Wi-Fi network. In still another embodiment, an antenna may receive an analog or digital terrestrial television signal from a transmitter. However, the television program may be received in the intermediary device in any manner, and the intermediary device may be integrated with the receiving device, in some approaches.

An amount of available storage space on each of at least two recording devices is determined in one approach. See operation 304. Any known method may be used to determine the amount of available storage space. In one approach, a storage manager may be queried to determine an amount of storage space that is marked as available for receiving data. In another approach, a total amount of space available, that may generally be output to a display device, e.g., to show a user how much capacity remains on the recording device, may be shown. In other approaches, a remaining amount of space and/or a used amount of space may be output, such as on a display device (e.g., a monitor, an LCD screen on a mobile device, etc.), on a visual meter (e.g., a series of LCD lights which display a circular gauge, a linear gauge, etc.), etc.

In this and other embodiments, determining an amount of available storage space may include determining an amount of free and/or overwritable storage space. The amounts may be actual, e.g., 120 GB available for writing to, or relative, e.g., 25% free space. In other approaches, determining the amount of available storage space may include determining an amount of used storage space. The amounts may be actual, e.g., 380 GB of 500 GB used, or relative, e.g., 75% used space.

One of the recording devices is selected to store a representation of the television program on a computer readable medium associated with the respective recording device based on the determined amounts of available storage space on each of the at least two recording devices, in one embodiment. See operation 306. The representation may be a copy, a compressed file, a native format duplicate, etc. The selected recording device stores the representation of the television program, e.g., on a recording (storage) medium such as a hard disk drive (HDD), a Flash memory, a random access memory (RAM), etc. In one approach, the recording device having the most available storage space may be selected for storing the representation of the television program. In another approach, the recording device may be selected based on some other criteria, as would be known to one of skill in the art, such as availability, speed, processing capacity, reliability of the connection to the content provider and/or of the system, etc.

A representation of the television program may be stored (e.g., digital and/or analog) on a computer readable medium, such as a diskette, a Secure Digital (SD) Card, a SONY MEMORY STICK, a CD-ROM, a DVD-ROM, a BLU-RAY disc, ROM, FLASH memory, HDD, etc. See operation 308. The representation may be a duplicate, copy, or clone of the program as received from the source (e.g., raw data, data derived from the incoming signal, a reassembly of the program from incoming packets of data, etc.), a compressed version of the received program, a converted version of the received program (e.g., for compatibility with a handheld device, to maximize storage space, to reduce processing demands, etc.), an upconverted version of the received program (e.g., upconverting standard definition broadcasting 480i/p to 720i, 720p, 1080i, 1080p, etc.), and combinations thereof, etc. The present description may refer to recording and/or storing a television program. This statement is equivalent and interchangeable with recording and/or storing a representation of the television program.

The recording device may be selected without user input regarding the selection, in some embodiments. In other approaches, user input may be solicited, such as user-confirmation of the selection, etc. In further approaches, parameters and designations for selecting the recording device(s) may be received from a user. Of course, in any embodiment, user input may be solicited, and if not received or not received in a predetermined period of time, a default selection may be followed.

In this and other embodiments, at least one of the recording devices may be a digital video recorder (DVR). In some embodiments, both of the recording devices may be DVRs.

In preferred embodiments, the representation of the television program stored on the selected recording device may be viewable from another of the recording devices. For example, in this and any other embodiment, the television program data may be streamed or otherwise transferred from the recording device on which it is recorded to a second recording device, e.g. via a network and/or direct connection, for output by the second recording device. In another approach, the representation of the program, in whole or in part, may be transferred to a second recording device and stored thereon. Moreover, in some approaches, identities of television programs stored on the selected recording device may be viewable from another of the recording devices. For example, in this and any other embodiment, the television programs stored on a first recording device may be viewable, selectable, transferrable, deletable, accessible, etc., from a second recording device, e.g., in a list output by the second recording device to a display device. Such list in this or any other embodiment may include a merged list or separate lists showing which programs are stored on which recording device, etc. In some approaches, a cover art, a title page, a thumbnail picture, etc., may be displayed that is representative of each television program stored on either recording device, such that a user can quickly and conveniently search and access a desired stored television program.

Figure 4:
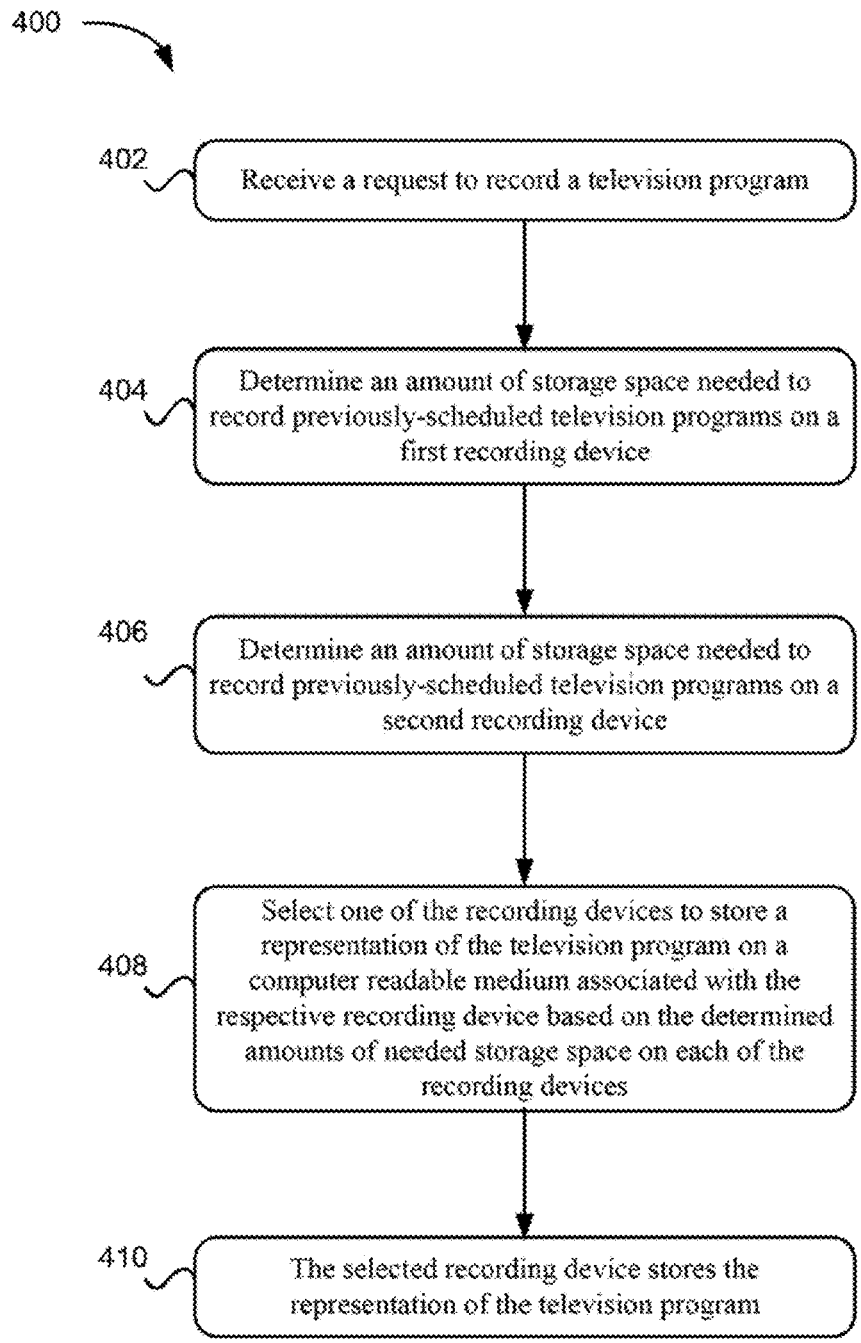
FIG. 4 is a flowchart depicting a system according to one embodiment.

A method 400 according to another embodiment depicted in FIG. 4 includes, or a system according to one embodiment has logic for, receiving a request to record a television program. See operation 402. The request and how it is received may be of any type, such as any one of the many exemplary types disclosed elsewhere herein.

An approximate or actual amount of storage space needed to record previously-scheduled television programs on a first recording device may be determined, according to one approach. See operation 404. Such previously-scheduled television programs may be determined from a "to do" list or queue, etc., of the first recording device. The amount of storage space may be approximated based on any factor or set of factors, such as length of the program, data size of previously-stored versions of programs in a series to which the requested program belongs, a data size received from the source of the program, a running time of the program, a compression ratio of the program, a definition of the program (e.g., 480i, 108i, 1080p, etc.), etc. In some embodiments, determining an amount of needed storage space includes estimating and/or determining an amount of data associated with the previously-scheduled television programs. The amount may be actual, e.g., 120 GB of data, or relative, e.g., will use 15% of the total available space.

Similarly, an approximate or actual amount of storage space needed to record previously-scheduled television programs on a second recording device may be determined. See operation 406.

One of the recording devices may be selected, with or without further user input, to store a representation of the television program on a computer readable medium associated with the respective recording device based on the determined amounts of needed storage space on each of the recording devices, where the selected recording device stores the representation of the television program. See operation 408 and 410.

In one approach, an amount of available storage space on each of the recording devices may be determined, and the selecting may further include determining whether a data size of the requested television program and the previously-requested television programs exceeds the amount of available storage space on each of the recording devices. If the total, data size exceeds the amount of available storage space on the first recording device but not on the second recording device, then the program may be recorded on the second recording device. If the total data size exceeds the available space on both recording devices, the program may be stored on the device that received the request, the user may be queried as to where to store the program, the program may be stored to the recording device having the most space available, the oldest recorded program (which can be deleted, with or without user input), etc.

In another approach, an amount of available storage space on each of the recording devices may be determined, and the recording device having the most available storage space may be selected for storing the representation of the television program. Further, the television program may be recording across both recording devices, such that a portion is recorded on the first recording device and a portion is recorded on the second recording device. The user can then watch the show in its entirety, since each recording device may access the content stored on the other recording device to output.

In yet another approach, if one or both recording devices do not have adequate free space to record the programs scheduled in a queue or "to do" list to record, one or both recording devices may search for alternate broadcast formats of the chosen television program from which to record the chosen television programs. For example, if a football game is selected to be recorded in 1080i high definition (HD), but there is not enough space on either recording device to store the entire football game in this HD format, then a standard definition (SD) broadcast may be chosen instead, and recorded by the recording device(s).

In preferred embodiments, the representation of the television program stored on the selected recording device may be viewable from another of the recording devices. For example, in this and any other embodiment, the television program data may be streamed or otherwise transferred from the recording device on which it is recorded to a second recording device, e.g. via a network and/or direct connection, for output by the second recording device, manipulation by the second recording device, transfer by the second recording device, etc. In another approach, the representation of the program, in whole or in part, may be transferred to a second recording device and stored thereon. Moreover, in some approaches, identities of television programs stored on the selected recording device may be viewable from the other recording devices. For example, in this and any other embodiment, the television programs stored on a first recording device may be viewable, selectable, transferrable, deletable, accessible, etc. from a second recording device, e.g., in a list output by the second recording device to a display device, etc. In some approaches, a cover art, a title page, a thumbnail picture, etc., may be displayed that is representative of each television program stored on either recording device, such that a user can quickly and conveniently search and access a desired stored television program.

Figure 5:
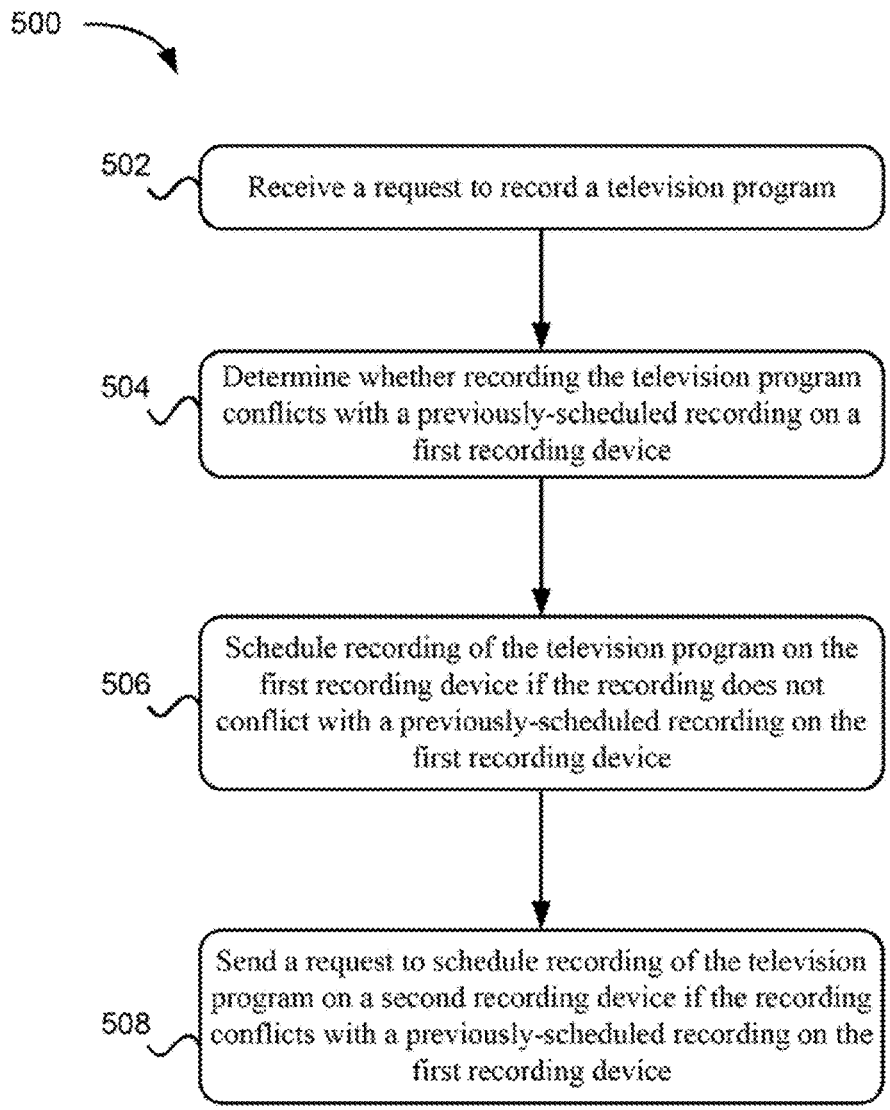
FIG. 5 is a flowchart depicting a system according to one embodiment.

A method 500 according to another embodiment depicted in FIG. 5 includes, or a system according to one embodiment has logic for, receiving a request to record a television program. See operation 502. The request may be of any type, and how the request is received may be via any technique, such as any one of the many exemplary types disclosed elsewhere herein.

A determination is made as to whether completing a recording of the television program may conflict with a previously-scheduled recording on a first recording device, in one approach. See operation 504. Such previously-scheduled recording may be determined from a "to do" list or queue, etc., of the first recording device. For recording devices having multiple tuners, and one tuner is available though the other tuner may be scheduled for use during the requested program, no conflict arises because the available tuner can be used, thereby avoiding the conflict. However, if all tuners are scheduled for use, then a conflict arises.

Recording of the television program may be scheduled on the first recording device if the recording does not conflict with a previousy-scheduled recording on the first recording device. See operation 506. If there is a conflict, then the recording may be scheduled to occur at a later time when a conflict will not arise, based on a later broadcast of the television program to be recorded.

A request to schedule recording of the television program on a second recording device may be sent if the recording conflicts with a previously-scheduled recording on the first recording device. See operation 508.

Preferably, the second recording device schedules recording of the television program upon receiving the request. However, a notification may be received from the second recording device that the recording conflicts with a previously-scheduled recording on the second recording device. Preferably, in such an event, a request for further instructions for recording the television program may be output. The request may include options such as canceling the request to record the television program, recording the television program at a later time, recording the television program on an alternate broadcast. etc. may be sent to a user. An alternate broadcast of the same television program may include, but is not limited to, broadcasts on other networks (ABC versus NBC, etc.), broadcasts at different times (10:30 PM versus 7:30 PM, etc.), broadcasts in different definitions (1080i versus 720p, etc.), broadcasts from different service providers (satellite service provider versus cable service provider, television programming available over the Internet versus television programming providers, etc.), etc. For example, if a television program conflicts with other scheduled recordings and cannot be recorded as scheduled, it may be downloaded from the Internet at a later time when there is space available on one or both recording devices.

The foregoing method may be performed by the first recording device, where the first recording device sends the request to schedule recording of the television program on the second recording device to the second recording device. Moreover, in some embodiments, the determining, scheduling, and/or sending operations may be performed without user input. The receiving operation, of course, may include receiving user input or operating under default settings in the case of a lack of user input.

In preferred embodiments, the representation of the television program stored on one recording device may be viewable from another of the recording devices. For example in this and any other embodiment, the television program data may be streamed or otherwise transferred from the recording device on which it is stored to a second recording device, e.g., via a network and/or direct connection, for output and/or manipulation by the second recording device. In another approach, the representation of the program in whole or in part, may be transferred to a second recording device and stored thereon. Moreover, in some approaches, identities of television programs stored on the selected recording device may be viewable from another of the recording devices. For example, in this and any other embodiment, the television programs stored on a first recording device may be viewable, selectable, transferrable, deletable, accessible, etc. from a second recording device, e.g., in a list output by the second recording device to a display device. In some approaches, a cover art, a title page, a thumbnail picture, etc., may be displayed that is representative of each television program stored on either recording device, such that a user can quickly and conveniently search and access a desired stored television program.

Figure 6:
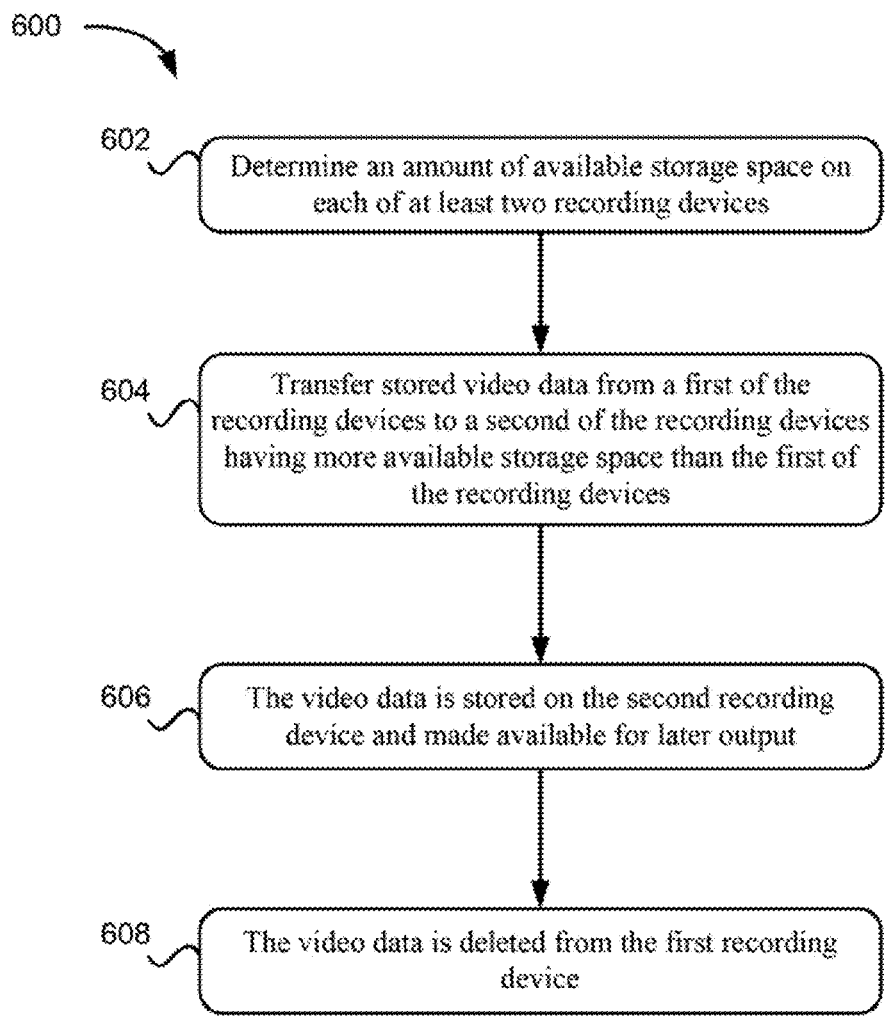
FIG. 6 is a flowchart depicting a system according to one embodiment.

A method 600 according to another embodiment depicted in FIG. 6 includes, or a system according to one embodiment has logic for, determining an amount of available storage space on each of at least two recording devices. See operation 602. Again, any method for determining the amount of available storage space may be used.

Stored video data may be transferred from a first of the recording devices to a second of the recording devices having more available storage space than the first of the recording devices. See operation 604. The transferred video data in any embodiment may be a clone, copy, duplicate, or replication of the data originally stored, a reduced quality or size version thereof, etc., for example, as described in U.S. patent application Ser. No. 12/362,966 to Kotab, filed Jan. 30, 2009, which is herein incorporated by reference.

The video data may be stored on the second recording device and made available for later output, and the video data may be deleted from the first recording device during or after the transferring. See operation 606 and 608. Among other things, this procedure opens up more recording space on the first recording device, thereby allowing the first recording device to operate as a primary storage device, while the second recording device captures overflow storage needs.

In one approach, the stored video data may be selected for transfer to provide about a same relative amount of storage space on the first and second recording devices after the transfer. For example, a first DVR may have 10% space available and a second DVR may have 40% space available before the transfer. After the transfer, both DVRs may have 25% space available.

in another approach, the stored video data may be selected for transfer to increase an amount of available storage space on the first recording device to at least a predetermined level. For example, the system may be set to keep at least 10% free space on the first DVR. When the first DVR has less than 10% free space, the foregoing process may occur automatically to transfer sufficient program data to the second DVR to provide the desired 10% free space availability on the first DVR.

In some embodiments, the stored video data may be transferred upon determining that a present or future recording operation will use more storage space than the available amount of storage space. For example, the process may be automatically invoked when the first DVR will, has, or is about to exceed a total amount of available storage space. Rather than requiring deletion of a previously-recorded program, e.g., the oldest program not flagged to keep, or not recording the currently-requested program, one or more stored television programs may be transferred to a second DVR for storage thereon. This may include the program being presently recorded. That way, the transferred program is not lost but remains available for viewing.

In one approach, the second recording device has a higher total data storage capacity than the first recording device, and the data is transferred to the second recording device because it has more capacity. For example, the second recording device may have a 2 GB hard drive, while the first recording device has a 500 MB hard drive.

In one embodiment, the process or system may further include receiving a selection of the stored video data for transfer; determining amounts of available storage space that each of the at least two recording devices would have after transfer of the selected video data; outputting the amounts of available storage space that each of the at least two recording devices would have after transfer of the selected video data; and receiving a further instruction to perform the transfer.

In another embodiment, the process or system may further include receiving a selection of the stored video data for transfer; determining amounts of available storage space that each of the at least two recording devices would have after transfer of the selected video data; outputting the amounts of available storage space that each of the at least two recording devices would have after transfer of the selected video data; receiving selection of different stored video data for transfer; determining and outputting amounts of available storage space that each of the at least two recording devices would have after transfer of the selected different video data; and receiving a further instruction to perform the transfer. Note that the different video data may be video data other than the video data first selected, or may include some or all of the video data first selected, along with newly-selected data.

In a particularly preferred approach, the recording device having the most available storage space may be selected for storing the representation of the television program.

In preferred embodiments, the representation of the television program stored on one recording device is viewable from another of the recording devices. For example, in this and any other embodiment, the television program data may be streamed or otherwise transferred from the recording device on which it is stored to a second recording device, e.g., via a network and/or direct connection, for output by the second recording device, in another approach, the representation of the program, in whole or in part, may be transferred to a second recording device and stored thereon. Moreover, in some approaches, identities of television programs stored on the selected recording device are viewable from the another of the recording devices. For example, in this and any other embodimen the television programs stored on a first recording device may be viewable, selectable, transferrable, deletable, accessible, etc., from a second recording device, e.g., in a list output by the second recording device to a display device. In some approaches, a cover art, a title page, a thumbnail picture, etc., may be displayed that is representative of each television program stored on either recording device, such that a user can quickly and conveniently search and access a desired stored television program.

The determining and transferring may be initiated without user input in one approach. For example, the method may be performed upon some triggering event, such as when a recording device determines that the storage capacity thereof is running low; at a predetermined time (e.g., scheduled maintenance); etc. In another approach, the method may be initiated upon receiving a user request.

Figure 7:
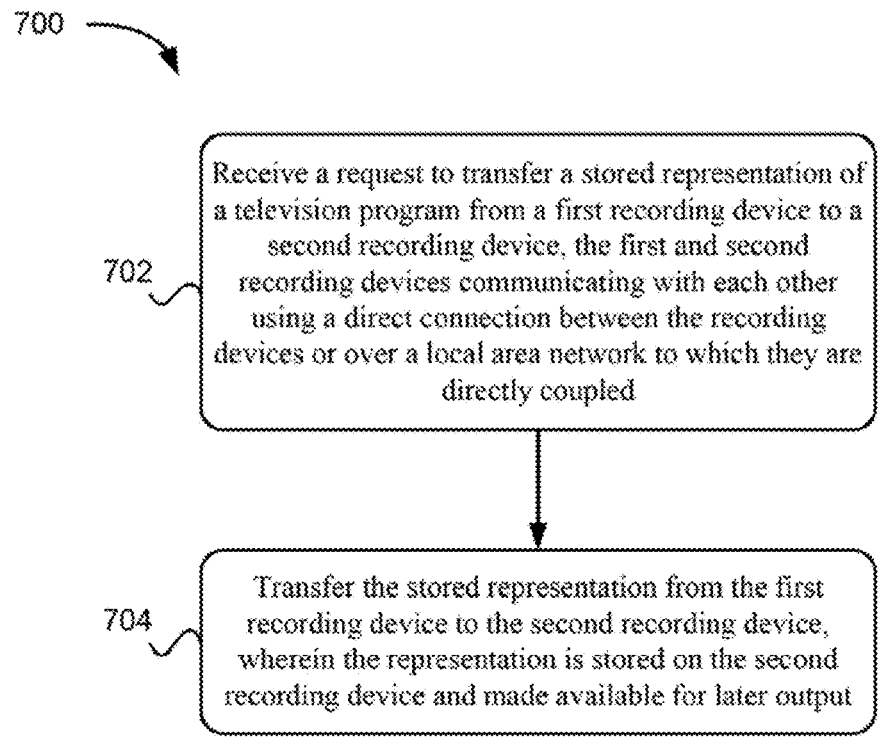
FIG. 7 is a flowchart depicting a system according to one embodiment.

A method 700 according to another embodiment depicted in FIG. 7 includes, or a system according to one embodiment has logic for, receiving a request to transfer a stored representation of a television program from a first recording device to a second recording device, the first and second recording devices communicating with each other using a direct connection between the recording devices or over a local area network to which they are directly coupled. See operation 702.

The stored representation is transferred from the first recording device to the second recording device, where the representation is stored on the second recording device and made available for later output. See operation 704. The video data may automatically (i.e., without further user input) be deleted from the first recording device during or after the transferring.

As an option, an amount of available storage space on each of the recording devices may be determined, and the amount of available storage space on each of the recording devices may be output, such as by displaying, transferring, copying, etc.

In preferred embodiments, the representation of the television program stored on the second recording device may be viewable from the first recording device. For example, in this and any other embodiment, the television program data may be streamed or otherwise transferred from the second recording device on which it is stored to the first recording device, e.g., via a network and/or direct connection, for output by the first recording device, e.g., to a television set, monitor, etc. In another approach, the representation of the program, in whole or in part, may be transferred to a second recording device and stored, thereon. Moreover, in some approaches, identities of television programs stored on the selected recording device are viewable from the another of the recording devices. For example, in this and any other embodiment, the television programs stored on a first recording device may be viewable, selectable, transferrable, deletable, accessible, etc. from a second recording device, e.g., in a list output by the second recording device to a display device. In some approaches, a cover art, a title page, a thumbnail picture, etc., may be displayed that is representative of each television program stored on either recording device, such that a user can quickly and conveniently search and access a desired stored television program.

Figure 8:
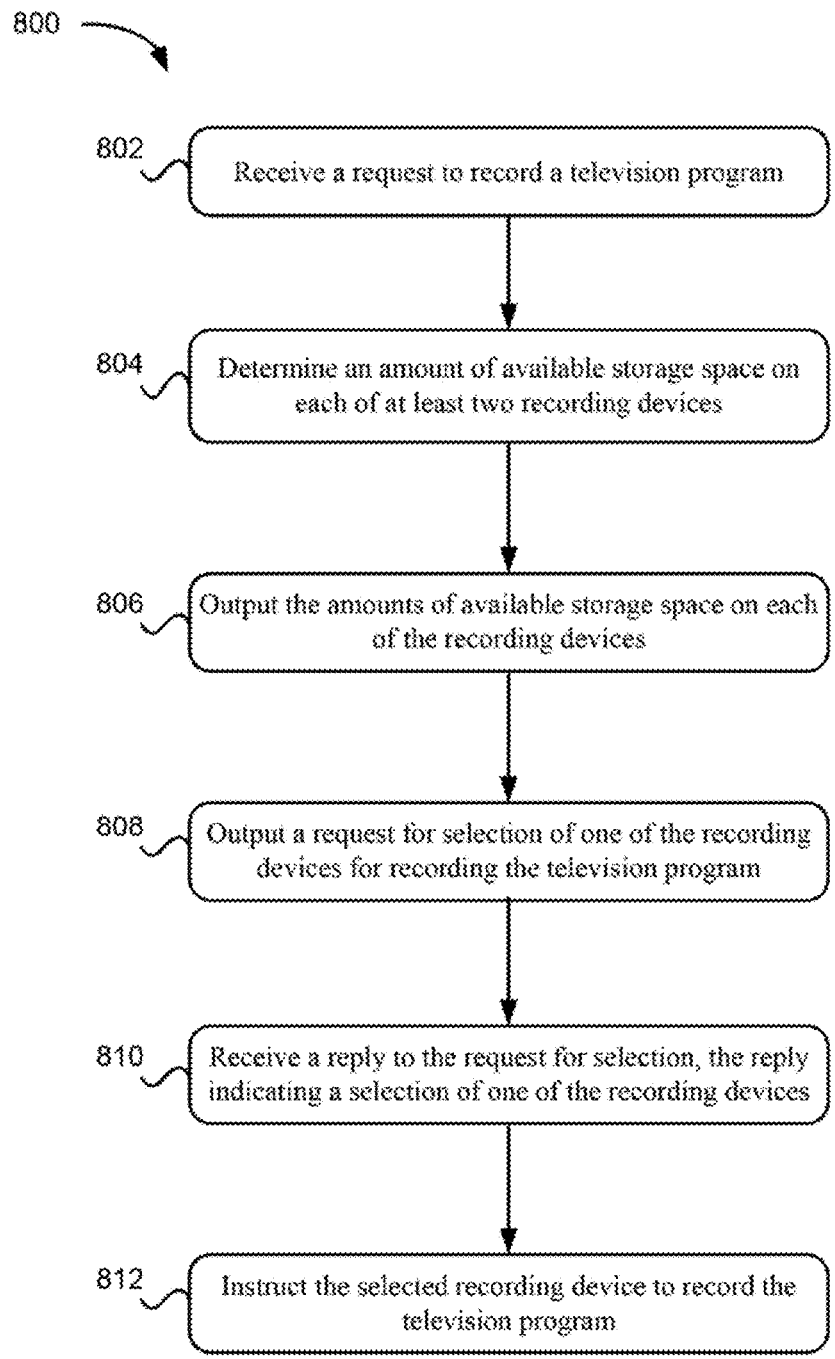
FIG. 8 is a flowchart depicting a system according to one embodiment.

A method 800 according to another embodiment depicted in FIG. 8 includes, or a system according to one embodiment has logic for, receiving a request to record a television program. See operation 802. The request may be of any type and how it is received may through any method, such as any one of the many exemplary types disclosed elsewhere herein.

An amount of available storage space on each of at least two recording devices may be determined. See operation 804. Again, any technique may be used to estimate the available storage space, including the exemplary methods disclosed herein.

The amounts of available storage space on each of the recording devices may be output and/or may be shared across each recording device. See operation 806.

A request for selection of one of the recording devices for recording the television program may be presented to a user for selection thereof, according to one embodiment. See operation 808.

A reply to the request for selection may be received. e.g., from a user, and the reply may indicate a selection of one of the recording devices for recording and/or accessing thereof according to another embodiment. See operation 810.

The selected recording device may be instructed to record the television program, in one embodiment. See operation 812.

In preferred embodiments, a representation of the television program stored on the second recording device is viewable from the first recording device. For example, in this and any other embodiment, the television program data may be streamed or otherwise transferred from the recording device on which it is stored to another recording device, e.g., via a network and/or direct connection, for output by the other recording device. In another approach, the representation of the program, in whole or in part, may be transferred to a second recording device and stored thereon. Moreover, in some approaches, identities of television programs stored on the second recording device are viewable from the first recording device. For example, in this and any other embodiment, the television programs stored on a first recording device may be viewable, selectable, transferrable, deletable, accessible, etc., from a second recording device and vice versa, e.g., in a list output by the recording device to a display device. In some approaches, a cover art, a title page, a thumbnail picture, etc., may be displayed that is representative of each television program stored on either recording device, such that a user can quickly and conveniently search and access a desired stored television program.

Figure 9:
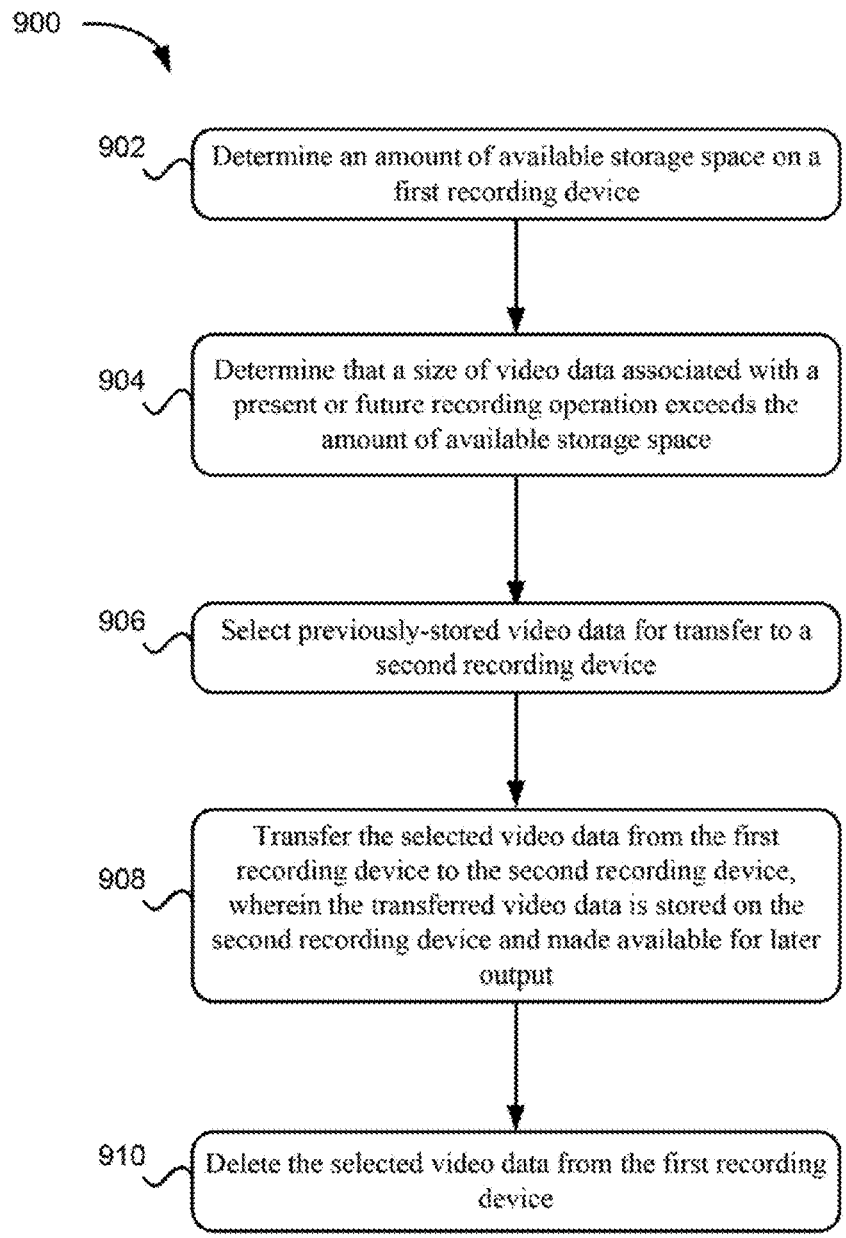
FIG. 9 is a flowchart depicting a system according to one embodiment.

A method 900 according to another embodiment depicted in FIG. 9 includes, or a system according to one embodiment has logic for, determining an amount of available storage space on a first recording device. See operation 902.

A determination may be made as to whether a size of video data associated with a present or future recording operation exceeds the amount of available storage space, in one embodiment. See operation 904.

If it is determined that the size of the video data associated with a present or future recording operation exceeds the amount of available storage space, previously-stored video data may be selected for transfer to a second recording device, e.g., to make room for the new recording, and/or deleted from the first recording device, in some embodiments. See operation 906.

The selected video data is transferred from the first recording device to the second recording device, where the transferred video data is stored on the second recording device and made available for later output. See operation 908. As an option, the selected video data may not be transferred to the second recording device if the second recording device does not have an amount of available storage space that is at least as great as a data size of the selected video data. In such case, other video data may be selected for transfer, video data may be deleted from the first recording device, etc. For example, the oldest recording not flagged to keep may be deleted. In another embodiment, a priority setting may dictate which video data is deleted and/or transferred. In another embodiment, duplicate recordings of television programs may be identified and one or more copies of the duplicate recordings may be deleted to maximize free space. See operation 910.

In one approach, the previously-stored video data is selected based on an amount of available storage space on the second recording device. For example, if the size of a first program is 4 GB and the size of a second program is 12 GB, and the second recording device has 10 GB of free space, the first program may be transferred. On the other hand, if the second recording device has 100 GB of free space, the larger program may be selected to provide more available free space on the first recording device.

The selected video data may be deleted from the first recording device during or after the transferring. The deleting may be performed by marking or listing the media space where the video data was stored as available for data storage, allowing overwriting of the transferred video data, etc. This procedure opens up more recording space on the first recording device without requiring absolute deletion of the video data.

In preferred embodiments, a television program associated with the video data transferred to the second recording device may be viewable from the first recording device. For example, in this and any other embodiment, the television program data may be streamed or otherwise transferred from the recording device on which it is stored to another recording device, e.g., via a network and/or direct connection, for output by the other recording device, e.g., viewing on a display, outputting via HDMI to another device, etc. In another approach, the representation of the program, in whole or in part, may be transferred to a second recording device and stored thereon. In alternative approaches, the storage may occur on a device connected to the second recording device, such as a portable HDD, a SD card, a USB drive, etc. Moreover, in some approaches, identities of television programs stored on the second recording device may be viewable from the first recording device. For example, in this and any other embodiment, the television programs stored on a first recording device may be viewable, selectable, transferrable, deletable, accessible, etc., from a second recording device and vice versa, e.g., in a list output by the recording device to a display device. In some approaches, a cover art, a title page, a thumbnail picture, etc., may be displayed that is representative of each television program stored on either recording device, such that a user can quickly and conveniently search and access a desired stored television program.

In various embodiments, the methodology presented herein may be performed by a recording device that is receiving instructions directly from a user, e.g., via a remote control, etc. In other approaches, the methodology presented herein may be performed at least in part on a second recording device that is receiving instructions directly from a user, the second recording device providing instructions to the first recording device to initiate some or all of the steps at the first recording device.

Additional embodiments are presented below. On skilled in the art, armed with the teachings herein, will appreciate that any of the features presented below may be combined with any of the features presented above to create the multitude of possible permutation and combinations falling within the spirit and scope of the present application.

Storage of television programming locally on a recording device is often problematic, in that the storage space thereon is limited, resulting in older programs being automatically deleted to make room for newer recordings.

Figure 10:
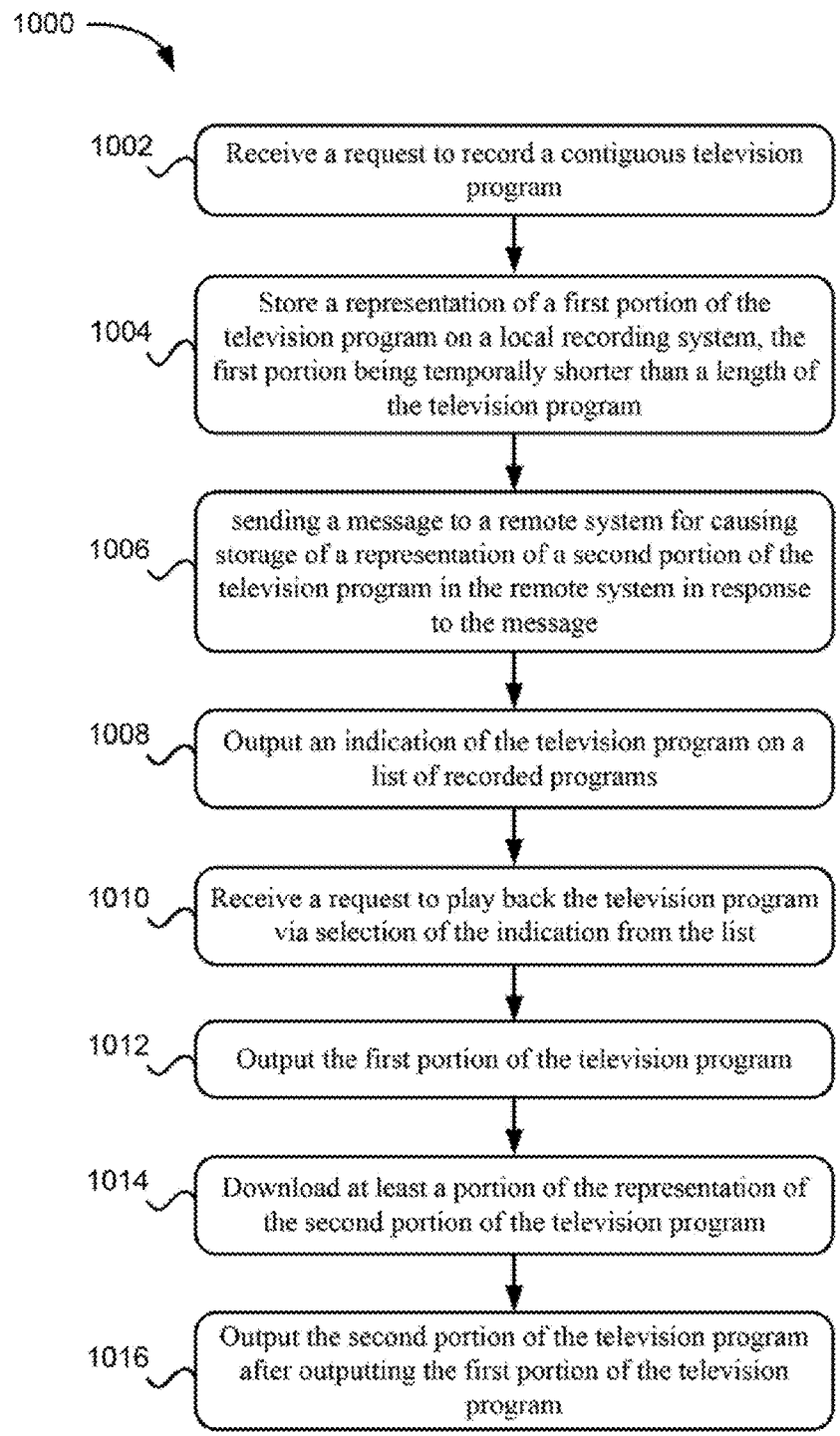
FIG. 10 is a flowchart depicting a system according to one embodiment.

Referring to FIG. 10, a method 1000 according to another embodiment includes, or a system according to one embodiment has logic for, receiving a request to record a contiguous television program, where "contiguous" refers to the program being broadcast in a single block of time such as 30 minutes, one hour, two hours, etc. on a single day for example. See operation 1002. Of course, presence of commercials, short interruptions or intermissions (e.g., up to about ½ hour in length), etc. daring the program may be considered to be part of the program, and would not alter the contiguous nature of the program.

The request to record the television program may be received via any suitable process or mechanism, including those presented elsewhere herein. For example, the request to record the television program may be received by the local recording system. In another example, the request to record the television program is received by a website and transferred to the local recording system.

In operation 1004, a representation of a first portion of the television program is stored on a local recording system such as the at the aforementioned recording device, any system implementing such a recording device as a component thereof, etc. For example, the local recording system may include any device, such as a storage unit such as a home storage server, personal computer, DVR, etc. and an output device coupled to the storage unit via a local network (e.g., LAN or WiFi network), the output device having an output connection for outputting the television program to a display device. In another embodiment, the local recording system is a digital video recorder. In a further embodiment, the local recording system includes a handheld device with integrated display.

The first portion of the television program is temporally shorter than a length of the television program. For example, the first portion can be fixed, e.g., the first 10 minutes, 15 minutes, 30 minutes, etc.; can be conditionally based on a contiguous length of the television program, e.g., first 10 minutes of a 30 minute contiguous program, first 20 minutes of a 60 minute contiguous program, etc.; can be conditionally based on a ratio or percentage, e.g., first 20% (temporally) of the contiguous program, first ¼ of the program, etc.; can be predetermined and/or selected by the recording device; can be selected by a user, e.g., correspond to a user-selected duration; can be specified by the content provider or recording device provider; may be based in part on genre, such as longer first portions for sports and shorter first portions for movies; etc.

In one approach, a duration of the first portion of the television program is based on an amount of available storage space on the local recording system. For example, if the available storage space is above some threshold such as 50%, 40%, 33%, etc., a longer first portion may be recorded. When the amount of available free space falls below that threshold, then a shorter first portion may be recorded. A sliding scale may be used in another approach, such as where the duration of the first portion, e.g. as a whole or at some ratio relative of the length of the program, becomes smaller in steps as the amount of available space decreases.

In operation 1006, a message is sent to a remote system for causing storage of a representation of a second portion of the television program in the remote system in response to the message. The second portion can be the portion of the television program remaining after the first portion, can include a small overlap of the first portion, can be some larger or smaller portion than the portion of the television program remaining after the first portion. etc. The message can be any type of data, such as data which includes a request to record the second portion, information about the program and the first portion thereof; a unique code that is interpreted by the remote system in a way that allows it to discern what to record; etc.

In most cases, the second portion of the television program is temporally shorter than a length of the television program, though it is envisioned that the entire program could be recorded by the remote system concurrently with only the first portion being recorded on the local recording system. Like the first portion, the duration of the second portion can be fixed, variable and/or conditional.

In one approach, the second portion of the television program corresponds to a portion of the television program that conflicts with another scheduled recording such as when the recording system has no available tuners to record the program. For example, assume a request is received to record program C from 7 pm to 8 pm. However, the recording system has two tuners, one of which is scheduled to record program A from 6 pm to 8 pm and the other of which is scheduled to record program B from 7:30 pm to 8 pm. Thus, a tuner is only available from 7 pm to 7:30 pm. The first portion of program C can be recorded locally until 7:30, at which time, recording of program B will commence. The second half of program C is stored by the remote system.

The remote system may be any type of system that is geographically removed from the local recording system and in constant, period, on demand, etc. communication with via any suitable mechanism such as a network connection, etc. Examples of a remote system may include, e.g., a client, network server, etc. In one approach, the remote system includes a server that the local recording system communicates with via the Internet. In another approach, the remote system includes a digital video recorder coupled to the local recording system via a local network (e.g., LAN or WiFi network).

In operation 1008, an indication of the television program is output on a list of (at least partially) recorded programs e.g., in a list output by a local recording device to a display device. The list, in this and any other embodiment, may include a sequential, sortable, etc. list of recorded programs, as well as assist in making the television programs stored on the local recording system viewable, selectable, transferrable, deletable, accessible, etc. Moreover, the list may be viewable from a second recording device, e.g., in a list output by the second recording device to a display device. Such list in this or any other embodiment may include a merged list or separate lists showing which programs are stored on which recording device and/or remote server, etc. In some approaches, a cover art, a title page, a thumbnail picture, etc., may be displayed that is representative of each television program stored on either recording device, such that a user can quickly and conveniently search and access a desired stored television program.

In operation 1010, a request to play back the television program is received via selection of the indication from the list. For example, a user browsing the list may select the program using a user interface device such as a remote controller, and then select a "play" button on the remote controller. In one approach, the local recording system receives signals associated with such user actions from the remote controller and initiates playback of the requested program using the stored representation of the first portion.

In operation 1012, the first portion of the television, program is output, e.g., to a display device such as a television. The local storage allows the first portion to be nearly instantaneously output to a display device. In other approaches, the first portion may be output to another system such as a set top box or second recording device coupled to the local recording system, etc. Thus, the representation of the television program stored on the local recording device may be viewable from another output device in communication therewith via a local network.

In operation 1014, at least a portion of the representation of the second portion of the television program is downloaded, e.g. while outputting the first portion of the television program, shortly thereafter, upon receiving a user request to download the second portion, etc.

Note that the representation of the second portion of the television program may be downloaded as stored at the remote system; may be modified, e.g., converted to a data format compatible with the recording device, compressed, etc.; etc. Preferably, the quality of the second portion upon playback is as good as the quality of the first portion.

In one embodiment, all of the representation of the second portion of the television program is downloaded. In one approach, once the user starts watching a program, the rest of the program can be simultaneously downloaded and stored on the local recording system so that it is ready for fast output to the display device, will not cause delays if the user fast forwards through portions of the program, etc.

In another embodiment, a portion of the representation of the second portion of the television program is downloaded. In one approach, about when output of the first portion program commences or shortly thereafter, a next temporal section of the program can be simultaneously downloaded and stored on the local recording system. The duration of the temporal section may be fixed, variable and/or conditional. For example, assume a 1 hour program is recorded, and the first portion includes the first 20 minutes of the program. Once the user selects the first program from the list or recorded programs and starts watching the first portion of the program, the local recording system downloads the next 20 minutes of the program. Once the user begins to watch the next 20 minutes of the program, the local recording system downloads the last 20 minutes of the program. In another example, a sliding temporal window may be used, such as in an embodiment where about 30 minutes of the program ahead of the temporal location currently being output to the user is stored on the local recording system. Data may be downloaded from the remote system as needed in order to keep about the sliding 30 minutes of the program available from the local recording system. If the user fast forwards the program to the point where the program is not locally stored, then the programming can be streamed from the remote system to the local recording system.

In operation 1016, the second portion of the television program is output after outputting the first portion of the television program. The second portion may be streamed directly to the display device, stored by the recording system and later output, etc. In further approaches, perhaps only a minute or two of the program is stored locally to enable instant playback, with the remaining portion stored remotely and downloaded immediately upon selection of the program or soon after the program is selected. In one preferred embodiment, downloading of the second portion of the television program is initiated about when playback of the first portion begins. In this way, a sizeable part of the second portion can be downloaded and stored by the local recording system before being output so that the dropped frames, lag, reduced quality, and/or pixilation typical of direct streaming of video is avoided. Note, however, that there may be some instances where video is directly streamed from the remote system and output, such as where the program is fast forwarded to a part thereof that is at the end of the portion stored on, or not yet stored on, the local recording system.

In one embodiment, an option to record the entire television program locally may be provided. Such option may be output for display along with other recording options. If the option is selected, the entire contiguous program may be recorded by the local storage system.

In some approaches, the request to record a contiguous television program may include a request to record a series of programs associated with the television program, and a specification of a duration of first portions of the programs in the series. Thus, for example, the user can dictate shorter first portions be stored in local storage for certain programs and/or series, perhaps for a series that the user is not sure he or she will watch, that the user knows he or she will not fast forward through, etc. The user may then also dictate longer first portions (and/or local storage of all of the program(s)) for other programs and/or series, for example, that the user may believe he or she will definitely watch, will be more apt to fast forward through, etc.

In one embodiment, a user request to delete the television program is received. In response thereto, the representation of the first portion and representation of the second portion of the television program may be deleted from the recording system upon receiving the request. In one approach, a delete message is sent to the remote system, the remote system deleting the representation of the second portion of the television program in response thereto. Note that this may occur at any time, including before any of the second portion is transferred to the recording system. Moreover, this may occur as a function of any type of criteria, such as the program passing an expiration or "delete by" date, the need to use the storage space allocated to the representation of the first portion, etc.

To conserve available recording space, the remote system may delete the at least a portion of the representation of the second portion of the television program upon transfer thereof, preferably immediately or shortly thereafter to free up storage space for further recordings.

Note that the local recording system may store non-television user data selected from a group consisting of photos, home videos, and documents on the local recording system.

Figure 11:
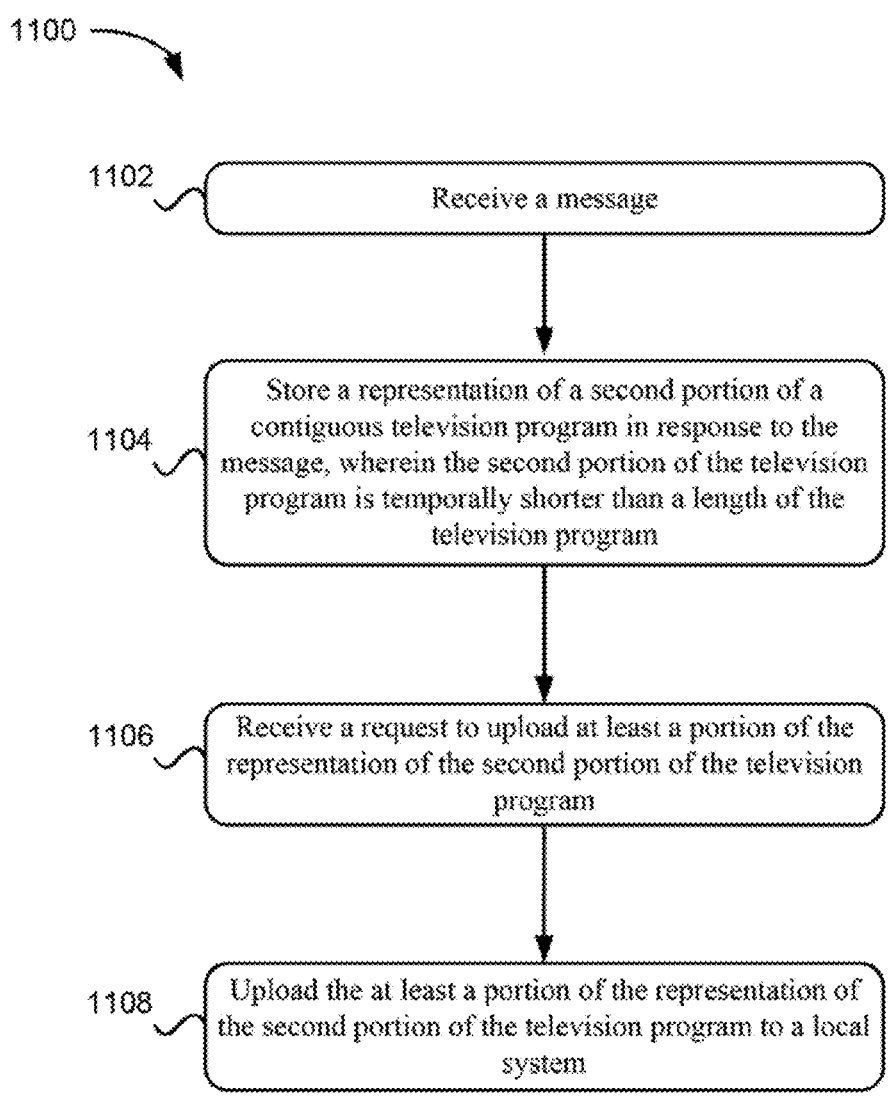
FIG. 11 is a flowchart depicting a system according to one embodiment.

FIG. 11 depicts a method 1100 that may be performed, for example, in association with logic of the remote system. As an option, such method may be implemented in the context of the architecture and environment of any of the foregoing FIGS. Of course, however, the methods may be carried out in any desired environment. Moreover, operations from the various methods may be combined in any desired manner to provide additional embodiments and permutations of the present invention.

In operation 1102, a message is received, e.g., from a local recording system that is located remotely and in communication therewith via a network such as the Internet. This message may be a message as noted above, or any other type of message that causes operation 1104 to be executed.

Moreover, the message may include a request to record a series of programs associated with the television program, and a specification of a duration of second portions of the programs in the series.

In operation 1104, a representation of a second portion of a contiguous television program is stored in response to the message, wherein the second portion of the television program is temporally shorter than a length of the television program. Thus, preferably, a representation of a first portion of the television program is not stored by the system performing the method 1100. However, the local system may record the first portion of the television program, where a duration of the first portion of the television program may be based on any of the parameters provided above.

The parameters relating to the second portion may be similar to those presented above for the first and/or second portions. For example, the second portion of the television program may correspond to a user-selected duration.

The representation of the second portion may be stored by any type of system, whether in a same household, halfway around the world, or somewhere in between. Thus, for example, the second portion may be a digital video recorder coupled to the local system via a local network (e.g., LAN or WiFi network).

In operation 1106, a request to upload at least a portion of the representation of the second portion of the television program is received, e.g., from the local recording system, from a server moderating the communications, etc.

In operation 1108, the at least a portion of the representation of the second portion of the television program is uploaded to a local system that may be any type of system such as the aforementioned local recording system, a storage unit such as a home storage server, personal computer, DVR, etc. and an output device coupled to the storage unit via a local network (e.g., LAN or WiFi network), a handheld device with integrated display, etc. The various portions and other components/parameters may be as described elsewhere herein. For example, the various durations can be fixed, variable and/or conditional. Thus, in one embodiment, all of the representation of the second portion of the television program is uploaded at one time, e.g., as part of the same transfer. In another embodiment, a portion of the representation of the second portion of the television program is uploaded at one time.

In one approach, the second portion of the television, program corresponds to a portion of the television program that conflicts with another scheduled recording on the local system.

In another approach, the at least a portion of the representation of the second portion of the television program is downloaded simultaneously with the outputting the first portion of the television program.

A request to delete the television program may be received, and the representation of the second portion of the television program deleted in response thereto.

Moreover, as above, the at least a portion of the representation of the second portion of the television program may be deleted upon transfer thereof.

Figure 12:
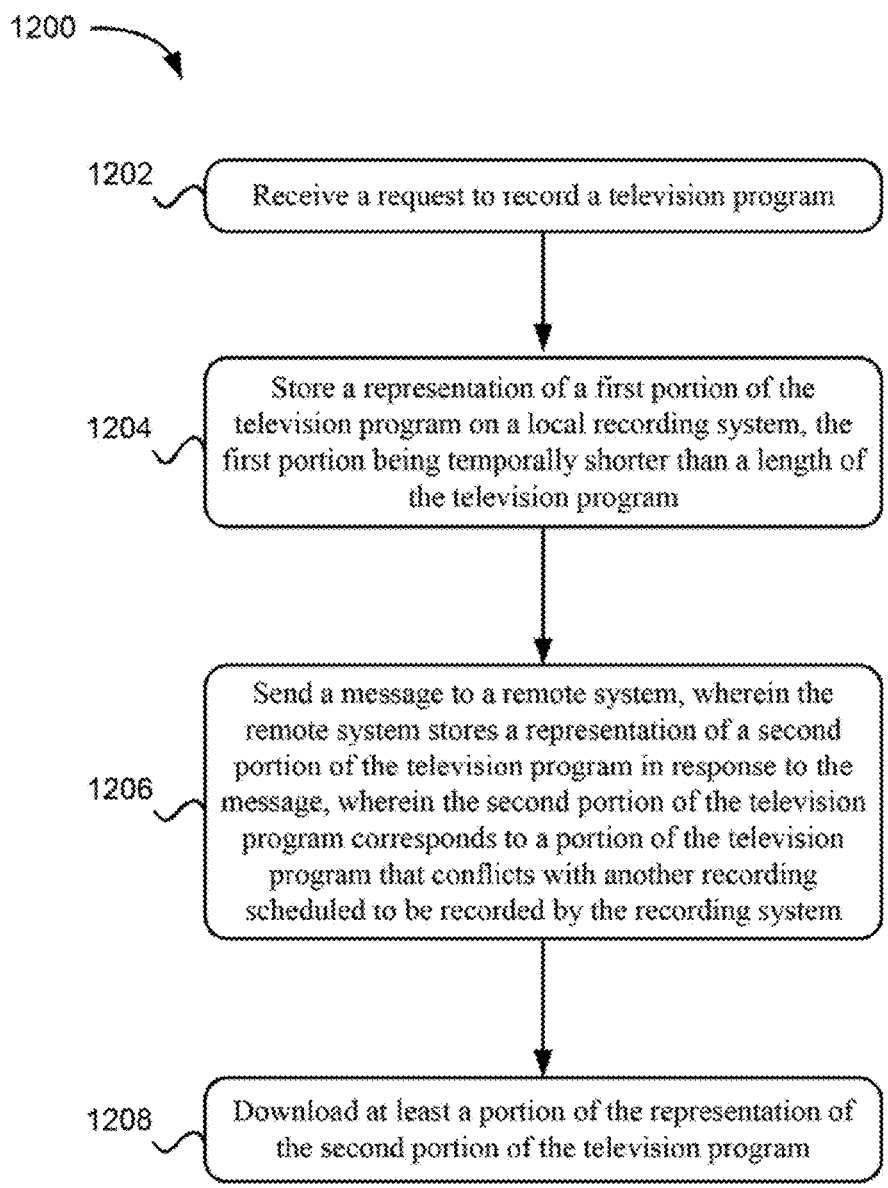
FIG. 12 is a flowchart depicting a system according to one embodiment.

FIG. 12 depicts a method 1200 according to one embodiment, or a system according to one embodiment having logic for performing the operations.

In operation 1202, a request to record a television program is received.

In operation 1204, a representation of a first portion of the television program is stored on a local recording system, the first portion being temporally shorter than a length of the television program.

In operation 1206, a message is sent to a remote system, where the remote system stores a representation of a second portion of the television program in response to the message, and where the second portion of the television program corresponds to a portion of the television program that conflicts with another recording scheduled to be recorded by the recording system.

In operation 1208, at least a portion of the representation of the second portion of the television program is downloaded.

Additional operations may be performed, such as one or more of outputting an indication of the television program on a list of (at least partially) recorded programs; receiving a request to play back the television program via selection of the indication from the list; outputting the first portion of the television program; and outputting the second portion of the television program after outputting the first portion of the television program.

In one embodiment, the at least a portion of the representation of the second portion of the television program is downloaded prior to outputting the first portion of the television program to a display device. For example, the representation of the second portion of the television program can be stored at least in a buffer at the remote system and streamed to the local recording system any time, e.g., as soon as the television program ends, before it ends, almost immediately upon receipt thereof by the remote system, etc.

In another embodiment, the at least a portion of the representation of the second portion of the television program is downloaded simultaneously with output of the first portion of the television program to a display device.

While the present invention has been illustrated and described with reference to specific embodiments, further modification and improvements will occur to those skilled in the art. The present description has thus been presented to enable any person skilled in the art to make and use the invention and is provided in the context of particular applications of the invention and their requirements. Various modifications to the disclosed embodiments will be readily apparent to those skilled in the art and the general principles defined herein may be applied to other embodiments and applications without departing from the spirit and scope of the present invention. Thus, the present invention is not intended to be limited to the embodiments shown or described, but is to be accorded the widest scope consistent with the principles and features disclosed herein.

In particular, various embodiments discussed herein may be implemented using the Internet as a means of communicating among a plurality of computer systems. One skilled in the art will recognize that the present invention is not limited to the use of the Internet as a communication medium and that alternative methods of the invention may accommodate the use of a private intranet, a LAN, a WAN, a PSTN or other means of communication. In addition, various combinations of wired, wireless (e.g. radio frequency) and optical communication links may be utilized.

The program environment in which a present embodiment of the invention may be executed illustratively incorporates one or more general-purpose computers or special-purpose devices. Details of such devices (e.g., processor, memory, data storage, input and output devices) are well known and are omitted for the sake of clarity.

It should also be understood that the techniques presented herein might be implemented in logic using a variety of technologies. For example, the methods described herein may be implemented in software (including firmware) running on a computer system, and/or implemented in hardware utilizing either a microprocessor and/or other specially designed application specific integrated circuits, programmable logic devices, and/or various combinations thereof. In particular, methods described herein may be implemented by a series of computer-executable instructions residing on a storage medium such as a disk drive, memory (RAM and/or ROM), or computer readable medium such as a nonvolatile computer readable storage medium, etc. Computer code enabling the methodology described herein may be downloadable. In addition, although specific embodiments of the invention may employ object-oriented software programming concepts, the invention is not so limited and is easily adapted to employ other forms of directing the operation of a computer.

Various embodiments can also be provided in the form of a computer program product comprising a computer readable medium having computer code thereon. A computer readable medium can include any medium capable of storing computer code thereon for use by a computer, including optical media such as read only and writeable CD and DVD, magnetic memory, semiconductor memory (e.g., FLASH memory and other portable memory cards, etc.), etc. Further, such software can be downloadable or otherwise transferable from one computing device to another via network, wireless link, nonvolatile memory device, etc.

Additionally, some or all of the aforementioned code may be embodied on any computer readable storage media including tape, FLASH memory, system memory, hard drive, etc. Additionally, a data signal embodied in a carrier wave (e.g., in a network including the Internet) can be the computer readable storage medium.

While various embodiments have been described above, it should be understood that they have been presented by way of example only, and not limitation. Thus, the breadth and scope of an embodiment should not be limited by any of the above-described exemplary embodiments, but should be defined only in accordance with the following claims and their equivalents.

What is claimed is:

1. A method, comprising:
    receiving a request to record a television program, the request being initiated by a local recording system;
    sending an indication of whether recording the television program conflicts with a previously-scheduled recording on a first recording device;
    sending a message to record the television program on the first recording device if the recording does not conflict with a previously-scheduled recording on the first recording device, the first recording device including a remote recording system;
    causing storage of a representation of the at least a portion of the television program in the remote recording system, in response to the message;
    outputting an indication of the television program on a list of recorded programs, the indication of the television program on the list of recorded programs being configured to be output on an integrated display associated with the local recording system;
    receiving a request to play back the television program via selection of the indication from the list, the request to play back the television program being initiated by the local recording system;
    outputting at least a first portion of the television program to the local recording system for display on the integrated display, while at least part of the representation of the at least a portion of the television program is being stored in the remote recording system, wherein a representation of the first portion of the television program is stored on the local recording system, the first portion being temporally shorter than a length of the television program;
    outputting at least a second portion of the television program to the local recording system for display on the integrated display, after outputting the first portion of the television program;
    in response to receiving a transfer request, allowing transfer of the entire television program to the local recording system, the complete version of the television program including at least the first portion of the television program and the second portion of the television program;
    allowing the storage of the entire television program by the local recording system;
    causing deletion of the representation of the at least a portion of the television program in the remote recording system, in response to receiving a request to delete the television program from the local recording system; and
    receiving a request to schedule recording of the television program on a second recording device if the recording conflicts with a previously-scheduled recording on the first recording device.

2. The method of claim 1, wherein the second recording device schedules recording of the television program upon receiving the request.

3. The method of claim 1, further comprising receiving a notification from the second recording device that the recording conflicts with a previously-scheduled recording on the second recording device.

4. The method of claim 3, further comprising outputting a request for further instructions for recording the television program.

5. The method of claim 1, wherein the method is performed by a gateway device.

6. The method of claim 1, wherein at least one of the recording devices is a digital video recorder.

7. The method of claim 1, wherein the request to record the television program is received by one of the recording devices.

8. The method of claim 1, wherein the request to record the television program is received by a website.

9. The method of claim 1, wherein a representation of the television program stored on the second recording device is viewable from the first recording device.

10. The method of claim 9, wherein identities of television programs stored on the second recording device are viewable from the first recording device.

11. The method of claim 1, wherein the sending a message to record operation is performed with user input.

12. A system, comprising:
    logic for receiving a request to record a television program, the request being initiated by a local recording system;
    logic for sending an indication of whether recording the television program conflicts with a previously-scheduled recording on a first recording device;
    logic for sending a message to record the television program on the first recording device if the recording does not conflict with a previously-scheduled recording on the first recording device, the first recording device including a remote recording system;
    logic for causing storage of a representation of the at least a portion of the television program in the remote recording system, in response to the message;

logic for outputting an indication of the television program on a list of recorded programs, the indication of the television program on the list of recorded programs being configured to be output on an integrated display associated with the local recording system;

logic for receiving a request to play back the television program via selection of the indication from the list, the request to play back the television program being initiated by the local recording system;

logic for outputting at least a first portion of the television program to the local recording system for display on the integrated display, while at least part of the representation of the at least a portion of the television program is being stored in the remote recording system, wherein a representation of the first portion of the television program is stored on the local recording system, the first portion being temporally shorter than a length of the television program;

logic for outputting at least a second portion of the television program to the local recording system for display on the integrated display, after outputting the first portion of the television program;

logic for, in response to receiving a transfer request, allowing transfer of the entire television program to the local recording system, the complete version of the television program including at least the first portion of the television program and the second portion of the television program;

logic for allowing the storage of the entire television program by the local recording system;

logic for causing deletion of the representation of the at least a portion of the television program in the remote recording system, in response to receiving a request to delete the television program from the local recording system; and logic for receiving a request to schedule recording of the television program on a second recording device if the recording conflicts with a previously-scheduled recording on the first recording device.

13. The system of claim 12, wherein the second recording device schedules recording of the television program upon receiving the request.

14. The system of claim 12, further comprising receiving a notification from the second recording device that the recording conflicts with a previously-scheduled recording on the second recording device.

15. The system of claim 14, further comprising outputting a request for further instructions for recording the television program.

16. The system of claim 12, wherein the method is performed by a gateway device.

17. The system of claim 12, wherein at least one of the recording devices is a digital video recorder.

18. The system of claim 12, wherein the request to record the television program is received by one of the recording devices.

19. The system of claim 12, wherein the request to record the television program is received by a website.

20. The system of claim 12, wherein a representation of the television program stored on the second recording device is viewable from the first recording device.

21. The system of claim 20, wherein identities of television programs stored on the second recording device are viewable from the first recording device.

22. The system of claim 12, wherein the sending a message to record operation is performed with user input.

23. A computer program product embodied on a non-transitory computer readable medium, comprising:

code for receiving a request to record a television program, the request being initiated by a local recording system;

code for sending an indication of whether recording the television program conflicts with a previously-scheduled recording on a first recording device;

code for sending a message to record the television program on the first recording device if the recording does not conflict with a previously-scheduled recording on the first recording device, the first recording device including a remote recording system;

code for causing storage of a representation of the at least a portion of the television program in the remote recording system, in response to the message;

code for outputting an indication of the television program on a list of recorded programs, the indication of the television program on the list of recorded programs being configured to be output on an integrated display associated with the local recording system;

code for receiving a request to play back the television program via selection of the indication from the list, the request to play back the television program being initiated by the local recording system;

code for outputting at least a first portion of the television program to the local recording system for display on the integrated display, while at least part of the representation of the at least a portion of the television program is being stored in the remote recording system, wherein a representation of the first portion of the television program is stored on the local recording system, the first portion being temporally shorter than a length of the television program;

code for outputting at least a second portion of the television program to the local recording system for display on the integrated display, after outputting the first portion of the television program;

code for, in response to receiving a transfer request, allowing transfer of the entire television program to the local recording system, the complete version of the television program including at least the first portion of the television program and the second portion of the television program;

code for allowing the storage of the entire television program by the local recording system;

code for causing deletion of the representation of the at least a portion of the television program in the remote recording system, in response to receiving a request to delete the television program from the local recording system; and code for receiving a request to schedule recording of the television program on a second recording device if the recording conflicts with a previously-scheduled recording on the first recording device.

* * * * *